United States Patent [19]

Sundermann et al.

[11] 4,388,246

[45] Jun. 14, 1983

[54] PROCESS FOR THE PREPARATION OF POLYISOCYANATES

[75] Inventors: Rudolf Sundermann; Klaus König, both of Leverkusen; Theodor Engbert, Dormagen; Gernot Becker, Dormagen; Günther Hammen, Dormagen, all of Fed. Rep. of Germany

[73] Assignee: Bayer Aktiengesellschaft, Leverkusen, Fed. Rep. of Germany

[21] Appl. No.: 354,687

[22] Filed: Mar. 4, 1982

[30] Foreign Application Priority Data

Mar. 10, 1981 [DE] Fed. Rep. of Germany ....... 3108990

[51] Int. Cl.³ .......................................... C07C 118/00
[52] U.S. Cl. ........................... 260/453 P; 260/453 SP
[58] Field of Search ....................... 260/453 P, 453 SP

[56] References Cited

U.S. PATENT DOCUMENTS

| | | | |
|---|---|---|---|
| 2,409,712 | 10/1946 | Schweitzer | 260/453 |
| 2,437,867 | 3/1948 | Verbanc | 260/453 SP |
| 2,692,275 | 10/1954 | Bortnick | 260/453 |
| 2,713,591 | 7/1955 | Bortnick | 260/453 |
| 2,727,020 | 12/1955 | Melamed et al. | 260/80.3 |
| 3,734,941 | 5/1973 | Sydor | 260/453 P |
| 3,919,278 | 11/1975 | Rosenthal et al. | 260/453 P |
| 3,919,279 | 11/1975 | Rosenthal et al. | 260/453 P |
| 3,962,302 | 6/1976 | Rosenthal et al. | 260/453 P |

FOREIGN PATENT DOCUMENTS 2625075 12/1977 Fed. Rep. of Germany .

54-39002 3/1979 Japan .

OTHER PUBLICATIONS

H. Schiff, Ber. der Dtsch. Chem. Ges., vol. 3, pp. 649-652.
A. W. Hofmann, Ber. der Dtsch. Chem. Ges., vol. 3, pp. 653-665.
Abbate et al., J. Appl. Pol. Sci., vol. 16, p. 1213.
Onodo et al., Chemical Abstracts, 91:5656g, (1979).
Houben-Weyl, "Methoden der organischen Chemie", Sauerstoffverbindungen III, 2. Auflage, 1952 Verlag, pp. 115-118.

*Primary Examiner*—Dolph H. Torrence
*Attorney, Agent, or Firm*—Gene Harsh; Joseph C. Gil; Lyndanne M. Whalen

[57] ABSTRACT

Polyisocyanates are prepared by thermally splitting a carbamate corresponding to the formula:

$$R^1(NH-CO-O-R^2)_n$$

in which $R^1$, $R^2$ and n are as defined herein into the corresponding isocyanate and alcohol. The splitting reaction is carried out at a temperature of from 150° to 350° C., at a pressure of from 0.001 to 20 bar and in the presence of an auxiliary agent. Suitable auxiliary agents are hydrogen chloride, organic acid chlorides, compounds having an alkylating effect and organotin (IV) chlorides. Inert solvents and catalysts may also be employed in the splitting products. The thus-produced isocyanate and alcohol are then separated, if necessary.

7 Claims, No Drawings

PROCESS FOR THE PREPARATION OF POLYISOCYANATES

BACKGROUND OF THE INVENTION

This invention relates to a process for the preparation of polyisocyanates by thermally splitting the corresponding carbamates. More specifically, it relates to a process in which the thermal splitting is carried out in the presence of an auxiliary selected from hydrogen chloride, inorganic and organic acid chlorides, compounds having an alkylation effect and organotin (IV) chlorides.

It is known that isocyanates may be made by the thermal splitting of carbamic acid esters (See, e.g., H. Schiff, Ber. der Dtsch. Chem. Ges., Vol. 3, p. 649 and A. W. Hofmann, Ber. der Dtsch. Chem. Ges., Vol. 3, p. 653). U.S. Pat. No. 2,409,712 describes a process in which the products formed by splitting carbamic acid esters are prevented from recombining either by rapid distillation of the product or by introduction of the product into a cyclohexane-water mixture. Although the process described is suitable for the preparation of isocyanates, it produces only moderate yields. Moreover, it is very expensive to practice on an industrial scale.

The processes disclosed in U.S. Pat. Nos. 3,962,302 and 3,919,278 are also carried out in a liquid phase (i.e., in the presence of inert solvents). In each of these processes, the thermal splitting of monofunctional and difunctional carbamic acid esters takes place in the absence of any type of additive in the inert, high boiling solvent. The products of the splitting reaction (i.e., isocyanate and alcohol) are distilled off continuously from the reaction medium and separately condensed. Such processes are disadvantageous in that only moderate volume-time yields can be obtained.

In order to increase the reaction rates, the use of basic catalysts has been proposed in German Auslegeschriften Nos. 1,016,699; 1,022,222 and 1,028,342. However, it is known (see, for example, J. Appl. Pol. Sci., Vol. 16, P. 1213) that the use of basic catalysts leads to increased formation of solid and insoluble by-products. Consequently, only moderate isocyanate yields are to be expected when a basic catalyst is used. Furthermore, the formation of solid by-products is extremely undesirable from a practical standpoint because sparingly soluble ureas and isocyanurates can lead to the blockage of pipes and other parts of the apparatus, with serious consequences. Moreover, carbon dioxide and gaseous olefins which are formed during the decarboxylation reaction of carbamic acid esters can cause pronounced gas charging of distillation columns.

The suppression of side reactions is particularly important during the preparation of nondistilling isocyanates (for example, polyisocyanate mixtures in the diphenyl methane series) because all non-volatile by-products will remain in the product isocyanate thereby reducing the quality of the isocyanate.

U.S. Pat. No. 3,919,279 and German Offenlegungschrift No. 2,635,490 describe processes in which the thermal splitting of carbamic acid esters is carried out in inert solvents and in the presence of metal catalysts. The use of these catalysts (primarily Lewis acids) generally results in yields which are higher than those achieved with basic catalysts. However, the problem of formation of undesirable by-products is not eliminated in either of these processes. Consequently, the above-mentioned processing disadvantages are also encountered when using these metal catalysts. These processes are subject to other serious disadvantages when non-distilling isocyanates are being produced because the catalysts used in the splitting operation remain in the splitting basin.

Japanese patent application No. 54-39002 (1979) discloses a process for the thermal splitting of TDI-bisethyl urethane which is carried out in an inert solvent in the presence of organic H-acidic compounds (for example β-diketones) without using metal catalysts. The formation of undesirable by-products would be expected to be prevented or substantially reduced by such additions of H-acidic compounds. In this process, however, only relatively small volume/time yields are possible due to the lack of effective catalysts. The economic feasibility of this process is therefore questionable.

SUMMARY OF THE INVENTION

It is an object of the present invention to provide a process for the production of polyisocyanates.

It is also an object of the present invention to provide a process for the production of polyisocyanates in improved yields in which formation of undesirable by-products is substantially reduced.

It is a further object of the present invention to provide an economically feasible process for the production of polyisocyanates in which formation of undesirable by-products is substantially reduced.

These and other objects which will be apparent to those skilled in the art are accomplished by thermally splitting a carbamate corresponding to the general formula

$$R^1(NH-CO-O-R^2)_n$$

in which $R^1$, $R^2$ and n are as defined below, into the corresponding isocyanate and alcohol. The splitting reaction is carried out at a temperature of from 150° to 350° C., at a pressure of from 0.001 to 20 bar and in the presence of an auxiliary agent. Suitable auxiliary agents are hydrogen chloride, organic acid chlorides, compounds having an alkylating effect and organotin (IV) chlorides. Inert solvents and catalysts may also be employed in the splitting process. The products of the splitting process are separated if necessary.

DETAILED DESCRIPTION OF THE INVENTION

The present invention relates to a process for the preparation of polyisocyanates or mixtures of polyisocyanates corresponding to the formula:

$$R^1(NCO)_n$$

by thermally splitting carbamates or mixtures of carbamates corresponding to the formula:

$$R^1(NH-CO-O-R^2)_n$$

wherein
$R^1$ represents an aliphatic hydrocarbon radical which may contain inert substituents and/or be olefinically unsaturated, with a total of from 2 to 18 carbon atoms; a cycloaliphatic hydrocarbon radical which may contain inert substituents and/or be olefinically unsaturated, with a total of from 3 to 18 carbon atoms; an araliphatic hydrocarbon radical which may contain inert substituents with a total of from 7 to 18 carbon atoms; or an aromatic hydrocarbon radical which may contain inert substituents with a total of from 6 to 27 carbon atoms;

$R^2$ represents a radical of the type obtained by removing the hydroxyl group from a primary or secondary aliphatic, cycloaliphatic or araliphatic alcohol which has a boiling point that is at least 10° C. below or above the boiling point of the polyisocyanate at normal pressure, and n represents 2 or an integer higher than 2.

R may represent different radicals within the above-given definition in the same molecule of carbamate. This thermal splitting may be carried out in the presence of inert solvents and/or catalysts. Temperatures of from 150° to 350° C. and pressures of from 0.001 to 20 bar are employed to split the carbamate. The polyisocyanates and alcohols produced as split products are then separated, if necessary. A key feature of the present invention is that the thermal splitting is carried out in the presence of auxiliaries selected from the group consisting of hydrogen chloride, organic acid chlorides, substances having an alkylating effect and organotin (IV) chlorides.

In the process of the present invention, it is preferable to use carbamates corresponding to the above-mentioned general formula in which:

$R^1$ represents a saturated aliphatic hydrocarbon radical with from 6 to 10 carbon atoms; a saturated cycloaliphatic hydrocarbon radical with from 6 to 15 carbon atoms; a xylyl radical or an aromatic hydrocarbon radical which may be methyl-substituted with a total of from 6 to 15 carbon atoms;

$R^2$ represents a primary or secondary aliphatic hydrocarbon radical with from 1 to 4 carbon atoms; and n represents 2.

When carbamates in which $R^1$ represents a diphenylene methane radical, of the type obtained by removing the isocyanate groups from diisocyanato diphenyl methane, and in which n represents 2, these carbamates can also be used in a mixture with higher homologs. Carbamate mixtures of this type may be formed, for example, during the acid catalyzed condensation of simple alkoxy carbonyl amino-substituted benzenes with formaldehyde.

Carbamates corresponding to the above-mentioned general formula which are most preferably used in the process of the present invention are those in which $R^1$ represents a radical of the type obtained by removal of the isocyanate groups from hexamethylene diisocyanate; 1-isocyanato-3,3,5-trimethyl-5-isocyanato methyl cyclohexane (isophorone diisocyanate); 2,4- and/or 2,6-diisocyanato toluene; 2,4'- and/or 4,4'-diisocyanato diphenyl methane or mixtures of the last-mentioned two isomers with higher nuclear homologues thereof (i.e. polyisocyanate mixtures of the diphenyl methane series) and $R^2$ represents a primary or secondary aliphatic hydrocarbon radical with from 1 to 4 carbon atoms.

Cycloaliphatic hydrocarbon radicals in the context of these definitions also include cycloaliphatic radicals containing aliphatic substituents and/or methylene bridges such as the hydrocarbon radicals forming the basis of isophorone diisocyanate or 4,4'-dicyclohexyl methane diisocyanate. Aromatic radicals in the context of these definitions include aromatic radicals interrupted by bridge members, for example, methylene groups, ether oxygen atoms or sulfone groups such as the radicals obtained by removing the isocyanate groups from 4,4'-diisocyanato diphenyl methane, 4,4'-diisocyanato diphenyl ether or diisocyanato diphenyl disulfone.

In the process of the present invention, it is preferable to use carbamates having an alcohol component $R^2$—OH which has a boiling point at least 40° C., most preferably at least 70° C. below or above the boiling point (at atmospheric pressure) of the polyisocyanate $R^1(NCO)_n$. These differences between boiling points in the split products simplify separation by distillation after the thermal splitting process. Carbamates having an alcohol component which boils below the boiling point of the polyisocyanate $R^1(NCO)_n$ at atmospheric pressure are generally used in the process of the present invention. The use of carbamates based on alcohols boiling at a higher temperature than the polyisocyanate is theoretically possible but impractical.

It is also possible to use mixtures of any carbamates corresponding to the above definitions in the practice of the present invention.

Specific examples of suitable carbamates include: 1,2-bis-(cyclohexoxycarbonylamino)-ethane; 1,4-bis-(ethoxycarbonylamino)-butane; 1,6-bis-(ethoxycarbonylamino)-hexane; 1,8-bis-(ethoxycarbonylamino)octane; 1-(methoxycarbonylamino)-6-(n-butoxycarbonylamino)-hexane; 1-(n-butoxycarbonylamino)-3,3,5-trimethyl-5-(n-butoxycarbonylamino-methyl)-cyclohexane; 1-(ethoxycarbonylamino)-3,3,5-trimethyl-5-(ethoxycarbonylamino-methyl)-cyclohexane; 1,4-bis-(ethoxycarbonylamino)-cyclohexane; 4,4'-bis-(ethoxycarbonylamino)dicyclohexylmethane; 4,4'-bis-(isopropoxycarbonylamino)dicyclohexylmethane; 1-methyl-2,4-bis-(ethoxycarbonylamino)-cyclohexane; 1,3-bis-(ethoxycarbonylamino)benzene; 1-methyl-2,4-bis-(ethoxycarbonylamino)-benzene; 1-methyl-2,4-bis-(ethoxycarbonylamino)-benzene; 1-methyl-2,4-(n-butoxycarbonylamino)-benzene; 1-methyl-2,6-bis-(ethoxycarbonylamino)-benzene; 1,5-bis-(ethoxycarbonylamino)-naphthalene; 1,3-bis-(ethoxycarbonylamino)-4-chlorobenzene; 1,4-bis-(ethoxycarbonylamino-methyl)benzene; 2,4'-bis-(ethoxycarbonylamino)-diphenylmethane; 2,4'-bis-(ethoxycarbonylamino)-diphenylmethane as well as any mixtures of these carbamates. Mixtures of carbamates in the diphenylmethane series are very well suited to the process of the present invention. Such mixtures include mixtures of the 2,4'- or 4,4'-bis-(alkoxycarbonylamino)-diphenylmethanes with corresponding higher nuclear homologs in which more than 2 alkoxycarbonylamino-substituted benzene rings are bonded together by methylene bridges. These carbamates mixtures of the diphenylmethane series may be formed during the acid-catalyzed condensation of simple alkoxycarbonyl-amino-substituted benzenes with formaldehyde.

The carbamates suitable to the process of the present invention may be produced by methods known to those in the art. In one such process, the corresponding polyamines are reacted with chloroformic acid esters. Other processes for producing such carbamates are: carbonylation of corresponding nitro compounds in the presence of alcohol; condensation of simple aromatic carbamic acid esters with formaldehyde or other aldehydes or ketones; and reaction of amines with urea and alcohols. The suitability of carbamates for the process of the present invention does not depend upon the method of production.

The process of the present invention is carried out in the presence of auxiliaries which are essential to the invention. These auxiliaries can also be called "stabilizers", i.e. compounds which counteract the undesirable side and secondary reactions. Suitable auxiliary compounds are hydrogen chloride, organic acid chlorides, substances which have an alkylating effect and organotin (IV) chlorides.

Appropriate organic acid chlorides include carboxylic acid chlorides having a molecular weight from 78 to 500, sulfonic acid chlorides having a molecular weight of from 114 to 500, and carbamic acid chlorides having a molecular weight of from 93 to 500.

Examples of carboxylic acid chlorides which may be used are: acetyl chloride, propionic acid chloride, butyric acid chloride, pentane carboxylic acid chloride, valeric acid chloride, lauric acid chloride, oleic acid chloride, stearic acid chloride, palmitic acid chloride, chloroacetic acid chloride, dichloroacetic acid chloride, chloropropionic acid chloride, 2-methyl-propionic acid chloride, 4-chlorobutyric acid chloride, 2-methylbutyric acid chloride, 3-methylbutyric acid chloride, dimethylpropionic acid chloride, 2-ethylbutyric acid chloride, 2-ethyl-hexanic acid chloride, methacrylic acid chloride, undecenic acid chloride, linoleic acid chloride, oxalyl chloride, succinic acid dichloride, glutaric acid dichloride, adipic acid dichloride, diethylmalonic acid dichloride, octane dicarboxylic acid dichloride, nonane dicarboxylic acid dichloride, trimethyladipic acid dichloride, decane dicarboxylic acid dichloride, dodecane dicarboxylic acid dichloride, heptadecane dicarboxylic acid dichloride, ethoxy acetic acid chloride, levulinic acid chloride, cyclohexane dicarboxylic acid dichloride, naphthane acid chloride, benzoic acid chloride, 2-chlorobenzoic acid chloride, 3-chlorobenzoic acid chloride, 4-chlorobenzoic acid chloride, 2,4-dichlorobenzoic acid chloride, 2,5-dichlorobenzoic acid chloride, 3,4-dichlorobenzoic acid chloride, 2-bromobenzoic acid chloride, 3-nitrobenzoic acid chloride, phenylacetic acid chloride, 4-chlorophenylacetic acid chloride, 2-methylbenzoic acid chloride, 3-methylbenzoic acid chloride, 4-methylbenzoic acid chloride, 4-tert.-butylbenzoic acid chloride, 3-phenyl-2-propene acid chloride, abietic acid chloride, 1-naphthalene carboxylic acid chloride, 2-naphthalene carboxylic acid chloride, biphenyl-4-carboxylic acid chloride, campheric acid dichloride, 5-norbornene-2,3-dicarboxylic acid dichloride, perchloro-5-norbornene-2,3-dicarboxylic acid dichloride, phthalic acid dichloride, isophthalic acid dichloride, terephthalic acid dichloride, tetrachlorophthalic acid dichloride, 4-chlorophthalic acid dichloride, 4-phenylphthalic acid dichloride, 1,1'-binaphthyl-8,8'-dicarboxylic acid dichloride, 1,3,5-benzenetricarboxylic acid trichloride, 1,2,4,5-benzenetetracarboxylic acid tetrachloride, 1,4,5,8-naphthalenetetracarboxylic acid tetrachloride, 2-hydroxybenzoic acid chloride, 2-methoxybenzoic acid chloride, 5-chloro-2-hydroxybenzoic acid dichloride, diphenylether-4,4'-dicarboxylic acid chloride, 3-chloro-4-hydroxybenzoic acid chloride and 4-hydroxyphthalic acid dichloride.

Sulfonic acid chlorides which may be used as an auxiliary compound in the practice of the present invention are: methane sulfonic acid chloride, chloromethane sulfonic acid chloride, chloroethane sulfonic acid chloride, perfluorobutane-1-sulfonic acid chloride, 4-chlorobutane-1-sulfonic acid chloride, benzene sulfonic acid chloride, 2-chlorobenzene sulfonic acid chloride, 3-chlorobenzene sulfonic acid chloride, 4-chlorobenzene sulfonic acid chloride, 2,5-dichlorobenzene sulfonic acid dichloride, 3,4-dichlorobenzene sulfonic acid dichloride, 2-nitrobenzene sulfonic acid chloride, 3-nitrobenzene sulfonic acid chloride, 4-nitrobenzene sulfonic acid chloride, 2-methylbenzene sulfonic acid chloride, 3-methylbenzene sulfonic acid chloride, 4-methylbenzene sulfonic acid chloride, 5-chloro-2-methylbenzene sulfonic acid dichloride, 3-chloro-4-methylbenzene sulfonic acid chloride, 2,4-dimethylbenzene sulfonic acid chloride, tetraline-6-sulfonic acid chloride, 1-naphthalene sulfonic acid chloride, 2-naphthalene sulfonic acid chloride, biphenyl-4-sulfonic acid chloride, pyrene-1-sulfonic acid chloride, benzene-1,3-disulfonic acid dichloride, xylene disulfonic acid dichloride, naphthalene-1,4-disulfonic acid dichloride, naphthalene-1,5-disulfonic acid dichloride, naphthalene-1,6-disulfonic acid dichloride, naphthalene-2,6-disulfonic acid dichloride, naphthalene-2,7-disulfonic acid dichloride, biphenyl-4,4'-disulfonic acid dichloride, naphthalene-1,3,6-trisulfonic acid trichloride, naphthalene-1,3,5,7-tetrasulfonic acid tetrachloride, pyrene-1,3,6,8-tetrasulfonic acid tetrachloride, 2-hydroxybenzene sulfonic acid chloride, 4-hydroxybenzene sulfonic acid chloride, diphenyl sulfone-3,3'-disulfonic acid dichloride, diphenylether-4,4'-disulfonic acid dichloride, 2,6-dichlorophenol-4-sulfonic acid chloride, phenol-2,4-disulfonic acid dichloride, benzoic acid chloride-2-sulfonic acid chloride, benzoic acid chloride-3-sulfonic acid chloride, 6-chlorobenzoic acid chloride-3-sulfonic acid chloride, benzoic acid chloride-3,5-disulfonic acid chloride, and phthalic acid dichloride-4-sulfonic acid chloride.

Examples of carbamic acid chlorides which may be used as auxiliary compounds include: N-methylcarbamic acid chloride, N-ethylcarbamic acid chloride, N-propylcarbamic acid chloride, N-isopropylcarbamic acid chloride, N-(2-methoxy-ethyl)-carbamic acid chloride, N-butylcarbamic acid chloride, N-(2-phenyl-ethyl)-carbamic acid chloride, N-pentyl-carbamic acid chloride, N-neopentylcarbamic acid chloride, N-hexylcarbamic acid chloride, N-(6-chlorohexyl)-carbamic acid chloride, N-octylcarbamic acid chloride, N-heptadecylcarbamic acid chloride, N-allylcarbamic acid chloride, N-cyclohexylcarbamic acid chloride, N-(2-cyclohexyl-cyclohexyl)-carbamic acid chloride, N-benzylcarbamic acid chloride, N-phenylcarbamic acid chloride, N-(3,4-dichlorophenyl)-carbamic acid chloride, N-3-tolylcarbamic acid chloride, N-(3-chloro-4-methyl-phenyl)-carbamic acid chloride, N-(cyclohexyl-phenyl)-carbamic acid chloride, N-(benzyl-phenyl)-carbamic acid chloride, N-naphthyl carbamic acid chloride, N-chloronaphthyl carbamic acid chloride, 1,4-butyl-dicarbamic acid chloride, 1,6-hexyl dicarbamic acid chloride, 1,8-octyl dicarbamic acid chloride, isophorone dicarbamic acid chloride, 1,4-cyclohexyl dicarbamic acid chloride, 4,4'-dicyclohexyl methane dicarbamic acid chloride, 2,4-(1-methylcyclohexyl)-dicarbamic acid chloride, 9,10-anthracene dicarbamic acid chloride, 1,5-naphthalene dicarbamic acid chloride, 1,3-benzene dicarbamic acid chloride, 1,4-benzene dicarbamic acid chloride, 2,4-toluene dicarbamic acid chloride, 2,6-toluene dicarbamic acid chloride, 1,3-(4-chlorobenzene)-dicarbamic acid chloride, 1,3,5-benzene-tricarbamic acid chloride, xylylene-dicarbamic acid chloride, and 4,4'-diphenylmethane dicarbamic acid chloride.

Examples of substances having an alkylation effect include sulfonic acid alkyl esters in the molecular weight range of from 110 to 500, dialkyl sulfates having a molecular weight of from 126 to 500, alkyl halides (including those which are olefinically unsaturated) having a molecular weight of from 50 to 500, esters of inorganic acids, and esters having an alkylation effect of organic acids.

Specific examples of sulfonic acid alkyl esters are: methane sulfonic acid methyl ester, benzene sulfonic acid methyl ester, toluene sulfonic acid methyl ester, fluoro sulfonic acid methyl ester, 1,8-naphthalene sulfone-6-sulfonic acid methyl ester and 4-ethoxycarbonyl benzoic sulfonic acid ethyl ester.

Dialkyl sulfates which are appropriate auxiliary compounds are dimethylsulfate, diethylsulfate and di-(n-hexyl)-sulfate.

Examples of optionally olefinically unsaturated alkyl halides include: methyl chloride, methyl iodide, ethyl iodide, ethyl bromide, isopropyl iodide, isopropyl bromide, tert.-butyl chloride, isobutyl chloride, isobutyl bromide, n-butyl bromide, 1,4-dichlorobutane, 1-chloro-3-methylbutane, n-hexyl chloride, n-hexyl bromide, n-hexyl iodide, n-heptyl chloride, dodecyl chloride, octadecyl chloride, octadecylbromide crotyl bromide, allyl bromide, allyl chloride, 3-chloro-2-methylpropene and 1,3-dichloro-2-butene.

Other esters having an alkylation effect of inorganic acids such as chlorosulfuric acid methyl ester, cyclohexyl bromide, cyclohexyl chloride, benzyl chloride, benzyl bromide, 4-methylbenzyl bromide, 4-methylbenzyl chloride, xylylene dichloride, xylylene dibromide, 2-chloro-2-phenyl propane and 6-chloromethyl tetraline are also appropriate auxiliary compounds. Esters having the alkylation effect of organic acids such as p-nitrobenzoic acid methyl ester, 3,4-dinitrobenzoic acid methyl ester and perfluorobutanic acid methyl ester may also be used.

Organotin (IV) chlorides such as dimethyl tin dichloride, diethyl tin dichloride, dibutyl tin dichloride, dihexyl tin dichloride, dioctyl tin dichloride, dibenzyl tin dichloride, dimethyl chloro tin-(2-ethylhexanoate), dibutyl chloro-octanoate, diethyl chloro tin acetate, dimethyl chloro tin oleate, dibutyl chloro tin laurate, triphenyl tin chloride, tributyl tin chloride and tribenzyl tin chloride are also useful as auxiliary compounds.

The auxiliaries, which are essential to the process of the present invention are generally used in quantities of from 0.001 to 5 wt. %, preferably from 0.01 to 1 wt. % (based on the total quantity of the reaction mixture including the solvent used). Which of these auxiliaries is preferred is a function of the reaction conditions and the structure of the carbamate to be split. It is generally desirable to add to the reaction mixture an auxiliary which is readily soluble in any solvent used, has a boiling point which ensures a sufficiently long residence time in the reaction mixture and is easily separated from the isocyanate to be prepared. This determination may be readily made by one skilled in the art. Particularly preferred auxiliaries include those having a boiling point which is at least 50° C. below or above that of the polyisocyanate to be prepared, at atmospheric pressure. This temperature difference is desirable because it ensures easy separation of the auxiliary from the product of the process. This restriction obviously need not be observed if the auxiliary used does not disturb the subsequent use of the product of the process.

The addition of the auxiliary to the carbamate to be split can be carried out by any one of several methods known to those in the art. Such methods include addition by means of a separate metering device or in any solvent used. When using hydrogen chloride or other auxiliaries with low boiling points, it is desirable to introduce these auxiliaries to the reaction mixture in gaseous form by itself or mixed with an inert gas which can perform the function of a carrier gas.

The process of the present invention may be carried out without solvents, particularly when using carbamates which are liquid under the reaction conditions. However, it is preferable to use an appropriate solvent. Suitable solvents include any compounds which are liquid under the processing conditions and which have a good dissolving capacity for the carbamate to be split and which are inert toward the carbamates and the split products of the invention. Solvents which have a boiling point of at least 150° C. at atmospheric pressure are particularly suitable. Such solvents include: substituted or unsubstituted aromatic hydrocarbons such as o-dichlorobenzene, dodecyl-benzene, biphenyl, terphenyl, 4-chlorobiphenyl, diphenyl-ether, biphenyl phenylether, phenanthrene, methylnaphthalene, chloronaphthalene, dichloronaphthalene, benzylnaphthalene, pentoxynaphthalene, dibenzyltoluene and dibenzylether; substituted and unsubstituted aliphatic hydrocarbons such as dodecane, octadecane, hexadecane, 1-chloro-octadecane, cetylchloride and stearylchloride; esters of organic and inorganic acids such as dibutylphthalate, dioctylphthalate, benzoic acid benzyl ester, phosphoric acid triphenyl ester; or sulfones such as diphenyl sulfone, phenyl tolyl sulfone, naphthyl phenyl sulfone, and tetramethylene sulfone.

The process of the present invention may be carried out by a variety of different methods. The specific method chosen will depend to some extent upon whether the polyisocyanate is obtained as a distillate or as a sump product.

When preparing sparingly volatile polyisocyanates, the carbamate to be split should be heated together with the auxiliary in a suitable reaction vessel at a pressure of from 0.001 to 20 bar (preferably from 0.01 to 1.5 bar) to 150° to 350° C. (preferably 180° to 280° C.). The auxiliary together with any other additives is generally used as a 1 to 50 wt. %, preferably 1 to 20 wt. % and most preferably as a 5 to 10 wt. % solution in one or more solvents of the type described above. It is preferable to use a reaction vessel provided with a reflux condenser and a solvent which boils under the above-mentioned temperature and pressure conditions. The solvent vapors produced in this process condense in the reflux condenser and flow back into the reaction vessel. The alcohol formed passes the reflux condenser (sometimes simultaneously with any carrier gas used) in the form of vapor and is thus removed from the reaction vessel. As soon as the splitting of the carbamate introduced has terminated, the solvent is removed by known methods (for example, by stripping distillation) and the polyisocyanate is obtained as a sump product. A simple boiler, for example, can be used as reaction vessel when the present invention is practiced on a batch basis.

In the preferred method for the continuous preparation of sparingly volatile polyisocyanate, the above-mentioned solution of the carbamate and of the auxiliary, as well as any other additives, is conveyed continuously into a reactor heated to a splitting temperature within the above-mentioned ranges and at a pressure within the above-mentioned pressure ranges. The alcohol formed is removed from the head of the reaction vessel (for example using a reflux condenser in which the solvent vapors condense) optionally with the aid of a carrier gas, and the product solution leaving the splitting reactor is worked up in a suitable manner. The working up operation is also preferably carried out in a continuous manner and can be undertaken by any suitable known method (for example, by distillation, thin layering or extraction).

The splitting reactor must be designed in such a way that the residence time in the reactor of the reactant solution is sufficiently long for complete splitting of the carbamate. Boilers arranged in a series are suitable for this purpose.

The auxiliaries essential to the practice of the present invention can be introduced into the reaction vessel generally in the above-mentioned quantities, as described, together with the solution of the carbamate. However, it is also possible to introduce the auxiliaries completely or partially by suitable metering devices, optionally after dilution with a solvent, into the reaction mixture. Thus it is possible to add a proportion of the auxiliary when the splitting of the carbamate is almost complete or to add it immediately before the working up process.

The thermal splitting of the carbamates in accordance with the present invention takes place within the above-mentioned pressure ranges but atmospheric pressure is preferred (with both the batch and continuous modes of operation). The working up of the product solution, however, is preferably carried out under vacuum (for example, at a pressure of from 1 to 50 mbar) in order to keep the thermal stress on the polyisocyanate as low as possible.

During the preparation of readily distilling polyisocyanates, it is possible to adopt a similar method to those described for the preparation of sparingly volatile polyisocyanates, but the product polyisocyanate should preferably not be left in the reaction medium until the completion of the splitting process. Rather, it is advantageous to distill the polyisocyanate together with the alcohol off from the reaction mixture immediately after the splitting process and to then separate the polyisocyanate from the alcohol in the vapor phase.

In one preferred method for producing polyisocyanates by the process of the present invention, the carbamate to be split is introduced as a solution or as a melt (optionally already mixed with the auxiliary essential to the invention) continuously into a splitting reactor charged with a suitable inert solvent and heated to the splitting temperature (within the above-mentioned ranges). The split products (i.e. the polyisocyanate and the alcohol) are removed from the reaction mixture continuously by adjusting the pressure and condensed selectively in a suitable apparatus. The reaction vessel used for this purpose can be a simple boiler above which there are arranged two reflux condensers connected in series, adjusted to different temperatures and which are both permeable to the more readily boiling split product. The uppermost reflux condenser should be maintained at a temperature between the boiling points of the polyisocyanate and the alcohol. The gaseous product mixture escaping at the head of the lower reflux condenser is partially condensed in the upper reflux condenser such that a mixture of the higher boiling split product and optionally small quantities of solvents or small quantities of material still containing urethane groups is produced as condensate. The more readily boiling split product escapes in gaseous form at the head of the upper reflux condenser. The lower reflux condenser generally arranged directly on the splitting reactor should have a lower temperature than the reaction medium so that the solvent (which is either boiling or entrained in the product stream) as well as carbamates and partially split carbamates which enter the gaseous phase are condensed, and flow back into the reaction vessel.

When the carbamate radical $R^2$ corresponds to the radical of a low boiling alcohol, the higher boiling isocyanate is condensed at the upper reflux condenser and the low boiling alcohol is obtained as a gaseous head product. This gaseous alcohol can be collected in a beaker which is cooled to a sufficiently low temperature.

Heat exchangers which are operated with liquid or gaseous cooling media (for example, water, heat-carrying oil or air) are generally used as reflux condensers suitable for the process according to the invention.

In order to remove the products formed during the splitting process as quickly and effectively as possible from the splitting reactor and in order to prevent recombination of polyisocyanate and alcohol in the reflux condenser system, it may be desirable to pass an inert gas or an inert liquid which boils at a low temperature under normal conditions through the reaction mixture. This inert fluid can subsequently be separated from the split products without difficulty.

It is generally desirable to use a solvent which just boils under the selected pressure and temperature conditions as the reaction medium.

The above-described process for the preparation of distilling isocyanates can be carried out under reduced or super atmospheric pressure in the range of from 0.001 to 20 bar. However, the splitting process is preferably carried out at a reduced pressure in the range of from 0.005 to 0.5 bar because this reduces the risk of recombination of the split products.

Pure isocyanate may be prepared from the crude condensate which contains mainly isocyanate by methods known to those in the art. One such technique is fractional distillation in separating columns. It may be advantageous to keep the temperature in the sump of the distillation columns below that prevailing in the splitting reactor because this prevents any thermal splitting of the carbamate present in the sump which splitting might reduce the effectiveness of the column and impair the purity of the distillate. Separation by distillation in the column generally takes place at a sump temperature of from 40° to 200° C., preferably from 80° to 160° C. and at a pressure of from 0.001 to 1.3 bar, preferably 0.005 to 1.1 bar.

The distillation residues produced during the purification by distillation of the isocyanates $R^1(NCO)_n$ contain carbamate and solvents as well as residual quantities of polyisocyanate. These residues can be recycled into the splitting reactor and again subjected to the splitting process. If it appears desirable, the alcohol $R^2OH$ can be separated from the crude condensate (which contains mainly the alcohol $R^2OH$) and obtained in pure form. The distillation residue thus formed (which again is essentially carbamate and solvents and residual quantities of alcohol) may be recycled into the splitting reactor and again subjected to the splitting process. If sparingly volatile by-products which remain in the reaction medium are formed to a slight extent during the described preparation of the distilling polyisocyanates, they can be separated from the reaction mixture in various ways. In one such method, after the concentration of the by-products in the reaction mixture has become too high, the supply of fresh carbamate is interrupted and the volatile constituents of the reaction mixture are removed as completely as possible from the splitting reactor by further distillation. The solvent containing the non-volatile by-products is then discharged and replaced by fresh or recovered solvent. The fresh or recovered solvent is preferably already preheated to the desired splitting temperature and may contain additives. If it appears necessary or desirable, the residue can also be extracted continuously from the reaction mixture. This can be accomplished by continuously removing the reaction solution from the splitting reactor and introducing a corresponding quantity of fresh or recovered solvent simultaneously.

The extracted solvent may be worked up by methods known in the art (for example by stripping distillation). It may be advantageous to carry out the distillation at a temperature above that in the splitting reactor because this reduces the risk of any residual quantities of carbamic acid ester remaining in the distillation sump. The solvent recovered by distillation can be recycled into the splitting reactor together with any concurrently distilled fractions of polyisocyanate and/or carbamate, and re-used as reaction medium. The auxiliaries essential to the invention can be added to the carbamate to be metered into the reaction vessel and/or can be introduced together with the solvent into the reaction vessel and/or can be metered into the reaction mixture by a separate metering device. The type and quantity of auxiliary essential to the invention depends upon the type of carbamate to be split, particularly on the type and quantity of impurities present therein. Such determination may be readily made by one skilled in the art.

The process of the present invention may also be carried out using additives (such as splitting catalysts) which are known to those in the art (e.g., those listed in German Offenlegungsschrift No. 2,635,490 or U.S. Pat. No. 3,919,279). These catalysts may be used in quantities of from 0.001 to 5 wt. %, preferably from 0.01 to 1 wt. % (based on the weight of the material located in the splitting reactor). It is preferable to use those catalysts having boiling points which lie clearly above the boiling points of the split products but which may be distilled together with the inert solvent used and thus recovered for further use. When preparing non-distilling polyisocyanates, it is advisable to use catalysts which can be easily and completely separated from any polyisocyanate remaining in the distillation sump (optionally together with the solvent) by distillation.

Having thus described our invention, the following examples are given by way of illustration. The percentages given in these examples relate to percentages by weight unless otherwise indicated.

EXAMPLES

Examples 1 to 9 illustrate continuous preparation of distilling polyisocyanates in the presence of the auxiliaries essential to the invention. Examples 10 to 13 demonstrate the preparation of sparingly volatile polyisocyanates in accordance with the present invention. All Examples designated by (a) are comparison examples in which the auxiliaries according to the invention were not used.

EXAMPLE 1

Molten 2,4-bis-(ethoxycarbonylamino)-toluene, to which 0.5 wt. % of isophthalic acid dichloride had been added was continuously introduced dropwise (at a rate of approximately 90 g/h) into a 2 liter four-necked flask filled with 500 g of naphthylphenyl sulfone that was equipped with an efficient stirrer, a device for discharging the solvent, two dropping funnels (which could be heated) and a device consisting of two temperature-controllable reflux condensers (for separating the gaseous split products after heating the naphthylphenyl sulfone acting as reaction medium to 250° C.).

The pressure in the splitting apparatus was adjusted so that the reaction medium heated to 250° C. boiled vigorously. This pressure was 7.5 mbar. The gaseous product mixture was partially condensed after passage through the first reflux condenser (which was adjusted to a temperature of 130° C. by means of heat-carrying oil) on which the solvent boiling with reflux condensed. On the upper reflux condenser (adjusted to a temperature of 20° C. with water), a product containing mainly 2,4-toluylene diisocyanate (TDI) was produced as condensate. This product was collected in a beaker located between the two reflux condensers. The gas mixture escaping at the head of the upper reflux condenser consisted essentially of ethanol and was collected in a beaker cooled to −60° C.

After ten hours, the supply of the carbamate was interrupted and no more product was condensed at the upper reflux condenser. The solvent was discharged and replaced by fresh solvent already preheated to the splitting temperature. The splitting of the carbamate was then continued for another ten hours.

Once a total of 1840 g of carbamate had been split in this way, the crude condensate consisting mainly of 2,4-toluylene diisocyanate was distilled over a packed column. 940 g ($\triangleq$78% of the theoretical yield) of pure 2,4-toluylene diisocyanate were obtained. 516 g ($\triangleq$81% of the theoretical yield) of pure ethanol were obtained upon distillation of the material in the beaker.

The distillation sumps, which consisted mainly of solvent, unreacted starting material (carbamate) and monoisocyanato monocarbamate (formed by eliminating 1 mol of ethanol from the carbamate) were re-used. An additional 150 g of 2,4-toluylene diisocyanate and an additional 86 g of ethanol were obtained by distillation of the crude condensates obtained in this process. 52 g of unchanged starting material (carbamate) and 46 g of monoisocyanato monocarbamate were still present in the distillation sumps.

To recover the solvent, the naphthylphenyl sulfone used was distilled at 250° C. and 5 mbar without a column. 105 g of a dark brown colored solid remained as residue. The recovered solvent consisted of 99.3 wt. % naphthylphenyl sulfone and 0.5 wt. % monoisocyanato monocarbamate.

The total quantity of starting carbamate which was present upon completion of the reaction (either unreacted or formed by recombination) was 52 g. The quantity of monoisocyanato monocarbamate formed by eliminating 1 mol of alcohol was 53 g. A selectivity of 96.7 mol % with respect to the diisocyanate formation was calculated, taking into consideration the total 1090 g of 2,4-toluylene diisocyanate ($\triangleq$91% of the theoretical yield) formed during the splitting process. The selectivity with respect to the ethanol production was 100 mol %.

The total non-distilling residue formed during the splitting reaction was 109 g. This corresponded to 10 wt. % (based on the quantity of diisocyanate formed).

EXAMPLE 1(a)

The process was carried out as described in Example 1, but without the addition of isophthalic acid dichloride. The results were as follows:

| | |
|---|---|
| Selectivity with respect to TDI formation | 92.1 mol % |
| Selectivity with respect to ethanol formation | 100 mol % |
| Residue based on the TDI formed | 30 wt. % |

EXAMPLE 2

1,500 g of 2,4-bis-(ethoxycarbonylamino)-toluene were split into TDI and ethanol in the manner described in Example 1. Diphenyl-tin-dichloride which was added to the solvent in a quantity of 0.5 wt. % (based on solvent) was used as auxiliary. The temperature in the splitting reactor was 200° C. and the pressure 5 mbar. Dibenzyl toluene was used as solvent. The results were as follows:

| | |
|---|---|
| Selectivity of TDI formation | 98.5 mol % |
| Selectivity of ethanol formation | 99.4 mol % |
| Residue based on the TDI formed | 1.5 wt. % |

EXAMPLE 2(a)

The process was carried out as described in Example 2, but 0.5 wt. % tin-II-dioctoate was added as catalyst instead of diphenyl-tin-dichloride. The results were as follows:

| | |
|---|---|
| Selectivity of TDI formation | 86.5 mol % |
| Selectivity of ethanol formation | 100 mol % |
| Residue based on the TDI formed | 32 wt. % |

EXAMPLE 3

2,4-bis-(ethoxycarbonylamino)-toluene was split into TDI and ethanol in accordance with the procedure described in Example 1. Isophthalic acid dichloride which was added to the carbamate in a quantity of 0.5 wt. % (based on carbamate) was used as auxiliary. In addition, 0.5 wt. % (based on solvent) of tin-II-dioctoate was added to the solvent. As in Example 2, dibenzyltoluene was used as solvent. As in Example 2, the temperature in the splitting reactor was 200° C. and the pressure was also 5 mbar. The results were as follows:

| | |
|---|---|
| Selectivity of TDI formation | 97.2 mol % |
| Selectivity of ethanol formation | 100 mol % |
| Residue based on the TDI formed | 12 wt. % |

EXAMPLE 4

The process described in Example 1 was followed using a mixture of 80% 2,4- and 20% of 2,6-bis-(ethoxycarbonylamino)-toluene as the starting carbamate.

Dimethyl chloro tin-(2-ethylhexanoate) which had been added to the solvent in a quantity of 0.1 wt. % (based on solvent) was used as auxiliary. Dibenzyltoluene was used as solvent. The temperature in the splitting reactor was 200° C. and the pressure 5 mbar. The results were as follows:

| | |
|---|---|
| Selectivity of TDI formation | 97.3 mol % |
| Selectivity of ethanol formation | 99.2 mol % |
| Residue based on the TDI formed | 3.1 wt. % |

EXAMPLE 5

Example 4 was repeated using a mixture of 65% of 2,4- and 35% of 2,6-bis-(ethoxycarbonylamino)-toluene and 0.3 wt. % (based on solvent) of the auxiliary of Example 4. The results were as follows:

| | |
|---|---|
| Selectivity of TDI formation | 99.7 mol % |
| Selectivity of ethanol formation | 100 mol % |
| Residue based on the TDI formed | 1.5 wt. % |

EXAMPLE 6

Example 4 was repeated using a mixture of the carbamates of Example 4 contaminated with 1 wt. % toluylene diamine (based on carbamate). The auxiliary mentioned in Example 4 was incorporated into the solvent in a quantity of 1.5 wt. % (based on the solvent). In addition, a 10% solution of isophthalic acid dichloride in dibenzyltoluene was continuously introduced dropwise into the reaction vessel during the splitting process so that a total of 0.75 wt. % of isophthalic acid dichloride was used (based on the total quantity of carbamate). The results were as follows:

| | |
|---|---|
| Selectivity of TDI formation | 96.1 mol % |
| Selectivity of ethanol formation | 99.3 mol % |
| Residue based on the TDI formed | 10 wt. % |

EXAMPLE 7

The process described in Example 1 was repeated using 1,6-bis-(ethoxycarbonylamino)-hexane as the starting carbamate. Dibenzyltoluene, to which 1 wt. % of diphenyl-tin-dichloride had been added was used as solvent. In addition, 0.2 wt. % (based on carbamate) of toluene sulfonic acid methyl ester was added to the carbamate. The temperature in the reactor was 200° C. and the pressure 5 mbar. The results were as follows:

| | |
|---|---|
| Selectivity of formation of hexamethylene diisocyanate (HDI) | 93.6 mol % |
| Selectivity of ethanol formation | 100 mol % |
| Residue based on HDI formed | 23 wt. % |

EXAMPLE 8

The process described in Example 1 was repeated using 1-(ethoxycarbonylamino)-3,3,5-trimethyl-5-(ethoxycarbonylamino-methyl)-cyclohexane as the starting carbamate. 0.05 wt. % of toluene sulfonic acid methyl ester was added to the carbamate. Dibenzyltoluene, to which 1 wt. % (based on solvent) of diphenyl-tin-dichloride had been added was used as the solvent. The reaction temperature was 200° C. and the pressure 5 mbar. The results were as follows:

Selectivity of formation of isophorone

| | |
|---|---|
| diisocyanate (IPDI) | 98.0 mol % |
| Selectivity of ethanol formation | 100 mol % |
| Residue based on IPDI formed | 3.9 wt. % |

EXAMPLE 9

Example 8 was repeated using a starting carbamate contaminated with 1 wt. % of isophorone diamine. The toluene sulfonic acid methyl ester was not added to the carbamate to be split, but was separately introduced dropwise into the splitting reactor as a 10% solution in dibenzyltoluene. The total quantity of toluene sulfonic acid methyl ester introduced was 0.6 wt. % (based on the starting carbamate). The results were as follows:

| | |
|---|---|
| Selectivity of IPDI formation | 95.8 mol % |
| Selectivity of ethanol formation | 99.5 mol % |
| Residue based on the IPDI formed | 12.6 wt. % |

EXAMPLE 10

A solution of 75 g of 4,4'-bis-(ethoxycarbonylamino)-diphenylmethane in 1425 g of diphenylether was heated to 250° C. at atmospheric pressure with intensive stirring and with addition of 0.5 g of terephthalic acid dichloride. During the splitting process, dried nitrogen was passed through the boiling reaction mixture at a rate of from 5 to 10 l/h. The alcohol formed was distilled over a column adjusted to 230° C. and collected in a cooled beaker. The conversion to isocyanate was determined by NCO titration of samples taken at half hour intervals.

The maximum NCO content of the reaction solution was obtained after 5 hours and was 1.23%. This corresponds to a selectivity of 98.9 mol %.

EXAMPLE 10(a)

The process described in Example 10 was repeated omitting the terephthalic acid dichloride. The selectivity of diisocyanate formation after four hours was 91 mol %.

EXAMPLE 11

The process described in Example 10 was repeated using a mixture of dicarbamates and polycarbamates of the diphenyl methane series containing 45 wt. % of trinuclear and higher nuclear carbamates (of the type obtained by condensation of ethoxycarbonylamino benzene with formaldehyde) as the starting material. 1.3 wt. % (based on the starting carbamate) of isophthalic acid dichloride was used as auxiliary essential to the invention. The selectivity of polyisocyanate formation after 4.5 hours was 100 mol %.

EXAMPLE 12

Example 10 was repeated, but using a starting carbamate contaminated with 1.3 wt. % (based on carbamate) of 4,4'-diamino diphenylmethane. 1.33 wt. % (based on starting carbamate) of isophthalic acid dichloride was used as auxiliary essential to the invention. The selectivity of diisocyanate formation after 3 hours was 96 mol %.

EXAMPLE 12(a)

Example 12 was repeated, but without using the auxiliary essential to the invention. The selectivity of diisocyanate formation after 3 hours was 77 mol %.

EXAMPLE 13

A 5% solution of a carbamate mixture from the diphenyl methane series with a content of 30 wt. % higher than binuclear carbamates (of the type obtainable by condensation of ethoxycarbonylamino benzene with formaldehyde) in diphenyl ether was preheated to 130° C. This solution was introduced at a rate of 1.0 l/h into a splitting reactor designed as a boiler cascade, of which the individual boilers joined together by laterally arranged overflow devices were heated to 250° C. A stream of dried nitrogen was simultaneously conveyed at a rate of about 7.5 l/h through the individual boilers.

The ethanol formed was expelled from the boiling reaction mixture in the nitrogen stream and was conveyed into cooled receivers over columns arranged immediately above the reaction boilers, adjusted to 230° C. and condensed therein.

Isophthalic acid dichloride was used as the auxiliary essential to the invention in a quantity of 1.0 wt. % (based on the carbamate). This auxiliary was added to the reaction mixture at the inlet to the first boiler and to the third boiler respectively. After 7 hours, the continuous splitting process was at equilibrium. The NCO content of the product solution leaving the fifth boiler was 1.18 wt. % at this time and for the following 5 hours. A selectivity of polyisocyanate formation of 99.5 mol % was calculated.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a polyisocyanate from a carbamate corresponding to the formula:

$$R^1(NH-CO-O-R^2)_n$$

wherein
R$^1$ represents an aliphatic hydrocarbon radical which may have inert substituents and/or be olefinically unsaturated with a total of from 2 to 18 carbon atoms; a cycloaliphatic hydrocarbon radical which may contain inert substituents and/or be olefinically unsaturated with a total of from 3 to 18 carbon atoms; an araliphatic hydrocarbon radical which may contain inert substituents with a total of from 7 to 18 carbon atoms; or an aromatic hydrocarbon radical which may have inert substituents with a total of from 6 to 27 carbon atoms;
R$^2$ represents a radical of the type obtained by removing the hydroxyl group from a primary or secondary aliphatic, cycloaliphatic or araliphatic alcohol having a boiling point which is at least 10° C. higher or lower than the boiling point of the polyisocyanate; and
n represents an integer greater than or equal to 2 comprising:
(a) thermally splitting the carbamate at a temperature of from 150° to 350° C. and pressure of from 0.001 to 20 bar in the presence of an auxiliary compound selected from the group consisting of hydrogen chloride, organic acid chlorides, compounds having an alkylating effect, organotin (IV) chlorides and mixtures thereof; and if necessary, (b) separating the thus-formed polyisocyanate and alcohol.

2. The process of claim 1 wherein the thermal splitting is carried out in the presence of an inert solvent.

3. The process of claim 1 wherein the thermal splitting is carried out in the presence of a catalyst.

4. The process of claim 1 wherein $R^1$ represents a saturated aliphatic hydrocarbon radical with from 6 to 10 carbon atoms, a saturated cycloaliphatic hydrocarbon radical with from 6 to 15 carbon atoms, a xylyl radical or an aromatic hydrocarbon radical which may have methyl substituents with a total of from 6 to 15 carbon atoms;

$R^2$ represents a primary or secondary saturated aliphatic hydrocarbon radical with from 1 to 4 carbon atoms; and n represents 2.

5. The process of claim 1 wherein $R^1$ represents a radical of the type obtained by removing the isocyanate groups from hexamethylene diisocyanate; 1-isocyanato-3,3,5-trimethyl-5-isocyanatomethyl-cyclohexane; 2,4-diisocyanatotoluene and/or 2,6-diisocyanatotoluene; 2,4'-diisocyanatodiphenylmethane and/or 4,4'-diisocyanatodiphenylmethane and/or mixtures of these two isomers with their higher homologs; and $R^2$ represents a primary or secondary saturated aliphatic hydrocarbon radical with from 1 to 4 carbon atoms.

6. The process of claim 5 wherein the auxiliary compound is used in a quantity of from 0.001 to 5 wt. %, based on the total reaction mixture.

7. The process of claim 1 wherein the auxiliary compound is used in a quantity of from 0.001 to 5 wt. %, based on the total reaction mixture.

* * * * *